United States Patent [19]

Itaya et al.

[11] 4,451,348
[45] May 29, 1984

[54] FUNCTIONAL ELECTRODE

[75] Inventors: Kingo Itaya, Tagajo; Kimio Shibayama; Shinobu Toshima, both of Sendai; Tatsuaki Ataka; Koji Iwasa, both of Tokyo, all of Japan

[73] Assignee: Kabushiki Kaisha Daini Seikosha, Tokyo, Japan

[21] Appl. No.: 456,790

[22] Filed: Jan. 10, 1983

[30] Foreign Application Priority Data

Jan. 12, 1982 [JP] Japan .................... 57-3044

[51] Int. Cl.³ .............. C25B 11/08; C25D 11/34; H01M 4/88
[52] U.S. Cl. ................ 204/290 R; 204/56 R; 204/292; 358/902
[58] Field of Search ............ 204/290 R, 56 R, 292; 358/902; 252/425.3

[56] References Cited

U.S. PATENT DOCUMENTS

| | | | |
|---|---|---|---|
| 1,911,808 | 5/1933 | Collins | 204/56 R |
| 2,312,898 | 3/1943 | Ham et al. | 204/56 R |
| 2,837,471 | 6/1958 | Law et al. | 204/56 R |
| 3,847,659 | 11/1974 | Sobajima et al. | 204/56 R |

*Primary Examiner*—Howard S. Williams
*Assistant Examiner*—Terryence Chapman
*Attorney, Agent, or Firm*—Robert E. Burns; Emmanuel J. Lobato; Bruce L. Adams

[57] ABSTRACT

A functional electrode is disclosed which is usable as an electrochromic display electrode, as a catalytic electrode effective to catalyze the evolution of oxygen and chlorine gases and the like. The electrode is composed of a conductor and a film deposited on the surface of the conductor, the film being comprised of a compound of the formula $M^I M(III)[M'(II)(CN)_6]$ or $M(III)_4[M'(II)(CN)_6]_3$ wherein $M(III)$ is $Fe(III)$, $Ru(III)$ or $Os(III)$, $M'(II)$ is $Fe(II)$, $Ru(II)$ or $Os(II)$ and $M^I$ is an alkali metal cation, with the proviso that said compound does not contain both $Fe(III)$ and $Fe(II)$. The functional electrode is produced by electrodepositing a compound of the formula $M^I M(III)[M'(II)(CN_6)]$ or $M(III)_4[M'(II)(CN)_6]_3$ on a conductor, from an aqueous solution containing $M(III)$ ions and $[M'(III)(CN)_6]^{3-}$ ions, wherein $M(III)$, $M'(II)$ and $M^I$ are as already defined and $M'(III)$ is $Fe(III)$, $Ru(III)$ or $Os(III)$, with the proviso that the aqueous solution does not contain both $Fe(III)$ and $[Fe(III)(CN)_6]^{3-}$ ions and the deposited compound does not contain both $Fe(III)$ and $Fe(II)$.

12 Claims, 2 Drawing Figures

FUNCTIONAL ELECTRODE

BACKGROUND OF THE INVENTION

This invention relates to films of Prussian blue analogs. More particularly, this invention relates to colored films synthesized by an electrochemical process on a material having electric conductivity at least at the surface.

The discussion of Prussian blue and Prussian blue analogs may most conveniently start from the explanation of Prussian blue which has been well studied with an past. Prussian blue is the compound that Diesbach, a dye craftsmany in Berlin first synthesized as a metal complex in 1704. Since then, Prussian blue has been widely used as a pigment for printing ink, paint and other coloring matter because of its deep blue color. Prussian blue has some interesting properties as well as being the first synthesized metal complex.

Prussian blue is believed to include two types of compounds that is, soluble Prussian blue $M^I Fe(III) [Fe(II)(CN)_6]$ and insoluble Prussian blue $Fe(III)_4[Fe(II)(CN)_6]_3$ wherein $M^I$ represents a monovalent cation. One of the interesting properties of Prussian blue of both type is that Fe(II) and Fe (III) differing in oxidation number coexist in a common crystal which appears deep blue and is an intrinsic semiconductor having a negative temperature coefficient of resistivity. Prussian blue is thus a typical mixed valence complex compound. The second interesting property of both types of Prussian blue is, that it is an insoluble salt having a solubility product $Ksp = 10^{-40}$ The third interesting property of Prussian blue is that Everitt's salt, a reduction product of Prussian blue which is represented by $M_2^I Fe(II) [Fe(II)(CN)_6]$ or $M_4^I Fe(II)_4[Fe(II)(CN)_6]_3$ and Berlin green, an oxidation product of product of Prussian blue which is represented by $Fe(III)[Fe(III)(CN)_6]$ or $Fe(III)_4[Fe(III)(CN)_6]_3 \cdot 3X^-$ wherein $X^-$ is a monovalent anion have the same crystalline structure as Prussian blue and a lattice constant of 10.2 angstrom (see, for example, J.F. Keggin and F.D. Miles, Nature, 137, 577(1936)). This means that the structure is not changed by an oxidation-reduction reaction.

The foregoing description refers to the interesting properties of Prussian blue as a typical example, and the same applies to Prussian blue analogs. For example, the compound having Ru(II) substituted for Fe(II) bonded to the carbon atoms of the cyano groups of Prussian blue is also a mixed valence complex which is known as a purple pigment designated ruthenium purple and has the same crystalline structure as Prussian blue and a lattice constant of 10.4 angstrom (see, for example, J.F. Keggin and F.D. Miles, 137, 577). This is also true for the compound having Os(II) substituted for Fe(II), which is known as a violet pigment.

Prussian blue and its analogs which have such interesting properties have, however, found no use other than as pigments for paint and ink because they have been available only in the form of colloidal powder. Prussian blue is prepared by a variety of processes, and typically by mixing an aqueous solution containing $Fe^{3+}$ with another aqueous solution containing $[Fe(CN)_6]^{4-}$. In this typical process, as expected from the solubility product, the reaction is completed to form a powdery product immediately after mixing, and as a result, neither a monocrystal nor a film is obtainable.

SUMMARY OF THE INVENTION

This invention is based on the finding of a novel method capable of forming a film of Prussian blue and its analogs, and an object of this invention is to substantially increase the range of application of these interesting compounds.

DETAILED EXPLANATION OF THE INVENTION

The following examples are illustrative of this invention.

EXAMPLE 1

This example is illustrative of a method for the synthesis of a film of ruthenium purple.

A commercial grade of $K_4Ru(CN)_6$ was dissolved in water to form an aqueous solution having a concentration of 10 mM. Oxidation of this solution with $H_2O_2$ resulted in an aqueous solution containing $[Ru(CN)_6]^{3-}$. To this solution was added an equimolar amount of a solution containing $Fe^{3+}$ at a concentration of 10 mM. It is to be noted that no deposit results from this mixed solution. A transparent electrode of 1 cm² in area formed on a glass substrate (NESA glass) and a plutinum plate electrode of about 10 cm² in area were immersed in this mixed solution, and galvanostatic electrolysis was carried out for about 5 minutes by supplying a current of 10 milliamperes with the transparent electrode as the cathode. After completion of the electrolysis, a purple film deposited on the transparent electrode was uniform in thickness and continuous. This purple film is comprised of $Fe(III)_4[Ru(II)(CN)_6]_3$ or KFe (III)[Ru(II)(CN)_6] that is iron (III) hexacyanoruthenate (II) salt.

EXAMPLE 2

This example demonstrates that the purple film obtained in Example 1 is the so-called ruthenium purple and useful as an electrochromic display material.

The purple film deposited on the transparent electrode in Example 1 was immersed in an aqueous solution of 0.5 M $K_2SO_4$. In addition, a counter electrode and a saturated calomel electrode (to be referred to as S.C.E., hereinafter) were placed in this solution to constitute a three electrode electrolytic cell. An absorption spectrophotometer was connected to the cell.

Figure 1:
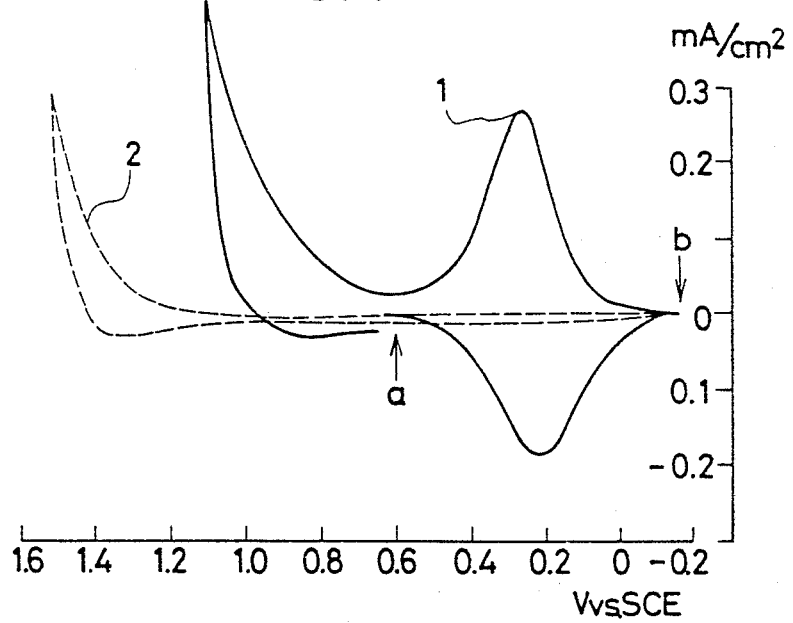
FIG. 1 shows the cyclic voltammograms of a ruthenium purple film electrode and a transparent electrode without any coating in an aqueous solution of 0.5 M $K_2SO_4$.

In FIG. 1, curve (1) shows the cyclic voltammogram of the purple film electrode. This test electrode was purple at a potential of $+0.6$ V vs. S.C.E. As the potential of the test electrode was swept to the cathodic direction, a reduction current peak appeared at about $+0.2$ V vs. S.C.E. and then the electrodde became transparent at $-0.2$ V vs. S.C.E. As the potential was swept to the anodic direction again, an oxidation current peak appeared at about $+0.2$ V and the electrode resumed its original purple color at $+0.6$ V.

Figure 2:
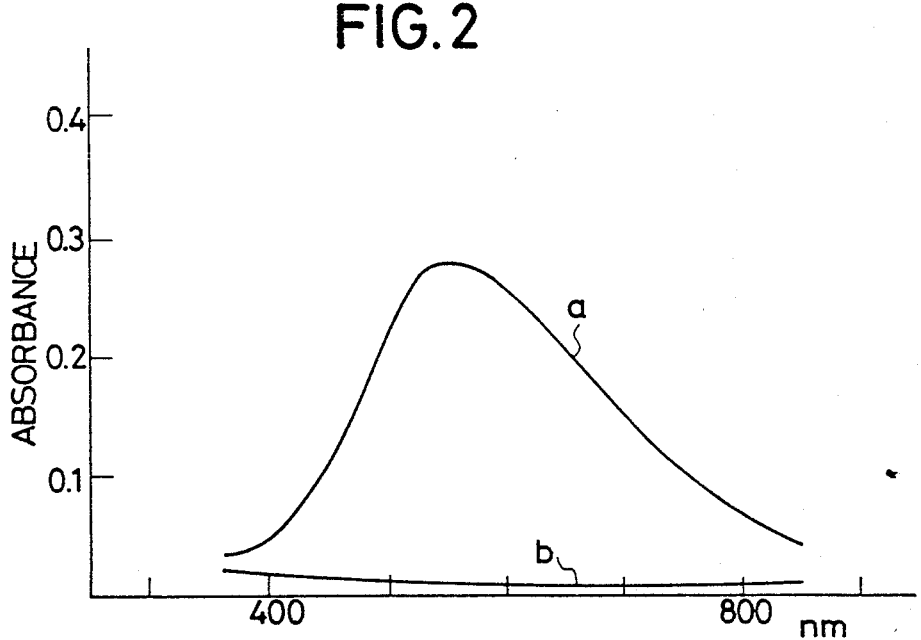
FIG. 2 shows the absorption spectra of a ruthenium purple film, curves a and b being the optical absorption spectra at $+0.6$ V and $-0.2$ V vs. S.C.E., respectively.

FIG. 2 shows the optical absorption spectrum measured for this test electrode at $+0.6$ V and $-0.2$ V vs. S.C.E. by means of the spectrophotometer connected to the cell. Curve a in FIG. 2 is the absorption spectrum at +0.6 V vs. S.C.E. which has an absorption peak at about 570 nm and coincides with that of ruthenium purple measured in a colloidal dispersion.

Curve b in FIG. 2 is the absorption spectrum at −0.2 V vs. S.C.E. which proves that there is no absorption in the visible region.

When the oxidation-reduction reaction was repeated on this test electrode by repeatedly changing the applied voltage between +0.6 V and −0.2 V vs. S.C.E., no change was observed on this electrode that is, a stable coloring and bleaching procedure was kept until the repetition number of $10^5$.

As this example demonstrates, the purple film deposited from a solution containing $Fe^{3+}$ and $[Ru(CN)_6]^{3-}$ is ruthinium purple and its electrode is useful as an electrochromic material displaying a purple color.

EXAMPLE 3

This example demonstrates that the film electrode of ruthenium purple used in Examples 1 and 2 is an effective catalyst for the evolution of oxygen and chlorine gases.

Curves (1) and (2) in FIG. 1 are cyclic voltammograms of the ruthenium purple film electrode and a transparent electrode, respectively.

As seen from curve (1) in FIG. 1, a substantial magnitude of oxidation current flows about +1.0 V. At the same time, evolution of oxygen gas from the electrode surface was observed. Curve (2) in FIG. 1 is the cyclic voltammogram of a transparent electrode without any coating and shows that evolution of oxygen gas takes place from about 1.4 V vs. S.C.E. This proves that the ruthenium purple film electrode is an effective catalyst for the evolution of oxygen gas.

Evolution of chlorine gas was detected at about 0.8 V vs. S.C.E. when the ruthenium purple film electrode was in 1 M KCl. This proves that the electrode is also an effective catalyst for the evolution of chlorine gas. Similar results were obtained from the ruthenium purple film electrodes with which platinum and glassy carbon plates were coated, respectively.

EXAMPLE 4

This example is illustrative of a method for the synthesis of a film of a compound having Ru(III) substituted for Fe(III) bonded to the nitrogen atoms of the cyano groups of Prussian blue.

An aqueous solution containing 10 mM of $RuCl_3$ and another aqueous solution containing 10 mM of $K_3Fe(CN)_6$ were mixed in equimolar amounts to form a brown clear solution. A transparent electrode of 1 $cm^2$ in area formed on a glass substrate and a glassy carbon plate electrode of about 10 $cm^2$ in area were immersed in the mixed solution, and galvanostatic electrolysis was carried out for about 5 minutes by supplying a current of 10 milliamperes with the transparent electrode as the cathode. After completion of electrolysis, a uniform, continuous, bluish-green film had deposited.

EXAMPLE 5

This example is illustrative of a method for the synthesis of a film of a compound having Os(II) substituted for Fe(II) bonded to the carbon atoms of the cyano groups of Purssian blue, and the usefulness of such a film as an electrochromic material.

By following the same procedures as in Example 1, a transparent electrode and a platinum counter electrode were immersed in a solution containing $Fe^{3+}$ and $[Os(CN)_6]^-$, and the transparent electrode was cathodically polarized at a currnet density of 10 $\mu A/cm^2$ to carry out galvanostatic electrolysis for about 5 minutes. A violet film deposited on the transparent electrode.

The violet film electrode in 1 M KCl was determined for cyclic voltammogram by the same procedure as in Example 2 to find that a stable oxidation-reduction cycle was repeated in which the electrode became violet at +0.6 V vs. S.C.E. and transparent at −0.2 V vs. S.C.E. This violet film is also useful as an electrochromic material. This violet film is comprised of KFe(III)-[Os(II) (CN)6] or $Fe(III)_4[Os(II) (CN)_6]_3$ that is iron (III) hexacyanoosmate (II).

EXAMPLE 6

This example is illustrative of a method for the synthesis of a film of a compound having Os(III) substituted for Fe(III) bonded to the nitrogen atoms of the cyano groups of Prussian blue.

As aqueous solution containing 10 mM of $OsCl_3$ and another aqueous solution containing 10 mM of $K_3Fe(CN)_6$ were mixed in equimolar amounts to form a clear brown solution. A glassy carbon plate electrode of 1 $cm^2$ in area and another glassy carbon electrode of 10 $cm^2$ in area were immersed in this mixed solution, and galvanostatic electrolysis was carried out for about 5 minutes by supplying a current of 10 milliamperees with the 1-$cm^2$ glassy carbon electrode as the cathode. A colored film deposited on the surface of the cathode.

The film represented by the general formula: $M^IM(III) [M' (II) (CN)_6]$ or $M(III)_4[M' (II) (CN)_6]_3$ and prepared by the method of this invention provides a compound with unknown, but remarkable properties, and thus is of great commercial value. For example, the films formed in the examples exhibit their own colors and are all useful electrochromic display materials.

What is claimed is:

1. A functional electrode usable as an electrochromic display electrode, as a catalyst electrode effective to catalyze the evolution of oxygen and chlorine, and the like comprising: a conductor having electric conductivity at least at the surface, and a colored film deposited on the surface of the conductor, wherein said colored film is comprised of a compound of the formula $M^IM(III)[M'(II) (CN)_6]$ or $M(III)_4 [M'(II) (CN)_6]_3$ wherein M(III) is Fe(III), Ru(III) or Os(III), M'(II) is Fe(II), Ru(II) or Os(II) and $M^I$ is an alkali metal cation, with the proviso that said compound does not contain both Fe(III) and Fe(II).

2. A functional electrode as set forth in claim 1 wherein the colored film is comprised of iron (III) hexacyanoruthenate (II) salt adhered to said conductor in an amount effective to exhibit electrochromic activity.

3. A functional electrode as set forth in claim 1 wherein the colored film is comprised of iron (III) hexacyanoruthenate (II) salt adhered to said conductor in an amount effective to exhibit electrochromic activity.

4. The functional electrode of claim 1 wherein said conductor is composed of transparent material.

5. A method of producing a functional electrode usable as an electrochromic display electrode, as a catalyst electrode effective to catalyze the evolution of oxygen and chlorine, and the like comprising: providing an aqueous solution containing M(III) ions and $[M'(III) (CN)_6]^{3-}$ ions, with the proviso that said solution does not contain both Fe(III) ions and $[Fe(II) (CN)_6]^{3-}$ ions; and electrodepositing a compound of the formula $M^IM-$ (III) [M'(II) (CN)$_6$] or M(III)$_4$[M'(II) (CN)$_6$]$_3$ on a conductor from said aqueous solution, wherein M(III) and M'(III) are each selected from Fe(III), Ru(III) or Os(III), [M'(III) is Fe(III), or Ru(III) or Os(III)] M'(II) is Fe(II), Ru(II) or Os(II) and M$^I$ is an alkali metal cation, with the proviso that said compound does not contain both Fe(III) and Fe(II).

6. A catalyst electrode effective to catalyze the evolution of oxygen and chlorine gases comprising: a conductor and a film deposited on the surface of the conductor, wherein said film is comprised of a compound of the formula M$^I$M(III) [M'(II) (CN)$_6$] or M(III)$_4$—[M'(II) (CN)$_6$]$_3$ wherein M(III) is Fe (III), Ru(III) or Os(III), M'(II) is Fe(II), Ru(II) or Os(II) and M$^I$ is an alkali metal cation, with the proviso that said compound does not contain both Fe(III) and Fe (II).

7. An electrochromic display element comprising: an electrode and a film of electrochromic material deposited on the surface of said electrode, wherein the electrochromic material is comprised of a compound of the formula M$^I$M(III) [M'(II) (CN)$_6$] or M(III)$_4$ [M'(II) (CN)$_6$]$_3$ wherein M(III) is Fe(III), Ru(III) or Os(III), M'(II) is Fe(II), Ru(II) or Os(II) and M$^I$ is an alkali metal cation, with the proviso that said compound does not contain both Fe(III) and Fe(II).

8. The electrochromic display element of claim 7 wherein said electrode is a transparent electrode.

9. A method for producing an electrochromic display element comprising: providing an aqueous solution containing M(III) ions and [Fe(II) (CN)$_6$]$^{3-}$ ions with the proviso that said solution does not contain both Fe(III) ions and [Fe(II) (CN)$_6$]$^{3-}$ ions; and electrodepositing a compound of the formula M$^I$M(III)[M'(II) (CN)$_6$] or M(III)$_4$[M'(II) (CN)$_6$]$_3$ on a conductor from said aqueous solution, wherein M(III) and M'(III) are each Fe(III), Ru(III) or Os(III), M'(II) is Fe(II), Ru(II) or Os(II) and M$^I$ is an alkali metal cation, with the proviso that said compound does not contain both Fe(III) and Fe(II).

10. The method of claim 9 wherein the conductor is composed of transparent material.

11. A method for producing a catalytic electrode effective to catalyze the evolution of oxygen and chlorine gases comprising: providing an aqueous solution containing M(III) ions and [M'(III) (CN)$_6$]$^{3-}$ ions, with the proviso that said solution does not contain both Fe(III) ions and [Fe(II) (CN)$_6$]$^{3-}$ ions; and electrodepositing a compound of the formula M$^I$M(III)[M'(II) (CN)$_6$] or M(III)$_4$—[M'(II) (CN)$_6$]$_3$ on a conductor from said aqueous solution, wherein M(III) and M'(III) are each Fe(III), Ru(III) or Os(III), M'(II) is Fe(II), Ru(II) or Os(II) and M$^I$ is an alkali metal cation, with the proviso that said compound does not contain both Fe(III) and Fe(II).

12. The functional electrode of claim 1 wherein either M(III) is Fe(III) or M'(II) is Fe(II).

* * * * *